(12) United States Patent
Yamamoto et al.

(10) Patent No.: US 12,343,206 B2
(45) Date of Patent: Jul. 1, 2025

(54) ULTRASOUND DIAGNOSTIC APPARATUS, CONTROL METHOD FOR ULTRASOUND DIAGNOSTIC APPARATUS, AND PROCESSOR FOR ULTRASOUND DIAGNOSTIC APPARATUS

(71) Applicant: FUJIFILM Corporation, Tokyo (JP)

(72) Inventors: Katsuya Yamamoto, Kanagawa (JP); Tomoki Inoue, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 177 days.

(21) Appl. No.: 18/062,472

(22) Filed: Dec. 6, 2022

(65) Prior Publication Data

US 2023/0108655 A1 Apr. 6, 2023

Related U.S. Application Data

(63) Continuation of application No. PCT/JP2021/008937, filed on Mar. 8, 2021.

(30) Foreign Application Priority Data

Jul. 1, 2020 (JP) .................................. 2020-114091

(51) Int. Cl.
*A61B 8/00* (2006.01)
*G10L 15/20* (2006.01)
*G10L 15/22* (2006.01)

(52) U.S. Cl.
CPC .......... *A61B 8/4427* (2013.01); *A61B 8/4488* (2013.01); *A61B 8/463* (2013.01);
(Continued)

(58) Field of Classification Search
CPC ..... A61B 8/4427; A61B 8/4488; A61B 8/463; A61B 8/467; A61B 8/54; A61B 8/4472; G10L 15/20; G10L 15/22; G10L 2015/223
See application file for complete search history.

(56) References Cited

U.S. PATENT DOCUMENTS 5,544,654 A * 8/1996 Murphy .................. A61B 8/00
704/E15.044
2002/0173721 A1* 11/2002 Grunwald .............. A61B 8/462
600/437

(Continued)

FOREIGN PATENT DOCUMENTS

JP H11-197142 A 7/1999
JP 2010-274049 A 12/2010
(Continued)

OTHER PUBLICATIONS

International Search Report issued in PCT/JP2021/008937; mailed Apr. 27, 2021.

(Continued)

*Primary Examiner* — Sean D Mattson
(74) *Attorney, Agent, or Firm* — Studebaker Brackett PLLC (57) ABSTRACT

In an ultrasound diagnostic apparatus (1), a normal screen display mode in which an ultrasound image and an operation panel for operating the ultrasound diagnostic apparatus (1) are displayed on a monitor (24) is set until a first voice is recognized, and a transition mode for transition from the normal screen display mode to a full-screen display mode in which an operation of the ultrasound diagnostic apparatus (1) using a voice is possible and only the ultrasound image is displayed on the monitor (24) is set in a case where the first voice is recognized. Further, the full-screen display mode is set in a case where the voice is recognized in the transition mode. The ultrasound diagnostic apparatus (1) is returned from the full-screen display mode to the normal screen display mode in a case where a predetermined second voice different from the first voice is recognized in the full-screen display mode.

4 Claims, 6 Drawing Sheets

(52) U.S. Cl.
CPC .............. *A61B 8/467* (2013.01); *A61B 8/54* (2013.01); *G10L 15/20* (2013.01); *G10L 15/22* (2013.01); *A61B 8/4472* (2013.01)

(56) References Cited

U.S. PATENT DOCUMENTS

| | | | |
|---|---|---|---|
| 2014/0052450 A1* | 2/2014 | Cheong | H04N 21/42203 704/E21.001 |
| 2016/0361044 A1* | 12/2016 | Hibi | A61B 8/54 |
| 2017/0071573 A1 | 3/2017 | Takahashi | |
| 2019/0336101 A1* | 11/2019 | Chiang | A61B 1/00 |

FOREIGN PATENT DOCUMENTS

| | | |
|---|---|---|
| JP | 2015-029791 A | 2/2015 |
| JP | 2015-231518 A | 12/2015 |
| JP | 2019-154623 A | 9/2019 |

OTHER PUBLICATIONS

Written Opinion of the International Searching Authority issued in PCT/JP2021/008937; mailed Apr. 27, 2021.

\* cited by examiner

ULTRASOUND DIAGNOSTIC APPARATUS, CONTROL METHOD FOR ULTRASOUND DIAGNOSTIC APPARATUS, AND PROCESSOR FOR ULTRASOUND DIAGNOSTIC APPARATUS

CROSS-REFERENCE TO RELATED APPLICATIONS

This application is a Continuation of PCT International Application No. PCT/JP2021/008937 filed on Mar. 8, 2021, which claims priority under 35 U.S.C. § 119(a) to Japanese Patent Application No. 2020-114091 filed on Jul. 1, 2020. The above applications are hereby expressly incorporated by reference, in its entirety, into the present application.

BACKGROUND OF THE INVENTION

1. Field of the Invention

The present invention relates to an ultrasound diagnostic apparatus, a control method for an ultrasound diagnostic apparatus, and a processor for an ultrasound diagnostic apparatus capable of performing voice recognition.

In the related art, an examination of the inside of a subject is performed using an ultrasound diagnostic apparatus. In such an examination, for example, as in a case where an ultrasound probe is fixed in one hand of a user and the inside of the subject is observed while the other hand of the user is used to insert a puncture needle into the subject, both hands of a user may not be available during an examination or a procedure using the ultrasound diagnostic apparatus. In order to operate the ultrasound diagnostic apparatus even in this state, for example, an ultrasound diagnostic apparatus that recognizes a voice of a user and controls an operation according to the recognized voice has been developed as disclosed in JP1999-197142A (JP H11-197142A).

SUMMARY OF THE INVENTION

On the other hand, for example, in a medical site at a remote place away from a hospital, such as a site for home nursing, a so-called handheld type ultrasound diagnostic apparatus including an ultrasound probe and a portable diagnostic apparatus main body connected to the ultrasound probe may be used. In such a handheld type ultrasound diagnostic apparatus, the diagnostic apparatus main body often includes a monitor with a touch sensor. The monitor of the handheld type ultrasound diagnostic apparatus has a small size in many cases, and it is necessary to display a user interface for allowing a user to perform an input operation on the monitor in addition to the captured ultrasound image. For this reason, as in the technique disclosed in JP1999-197142A (JP H11-197142A), even in a case where the user can perform an input operation by voice recognition, it may be difficult for the user to confirm the ultrasound image displayed on the monitor, and it may be difficult to smoothly perform ultrasound diagnosis.

The present invention has been made to solve such problems in the related art, and an object of the present invention is to provide an ultrasound diagnostic apparatus, a control method for an ultrasound diagnostic apparatus, and a processor for an ultrasound diagnostic apparatus capable of allowing a user to smoothly perform ultrasound diagnosis.

In order to achieve the above object, according to an aspect of the present invention, there is provided a handheld type ultrasound diagnostic apparatus including: an ultrasound probe; and a diagnostic apparatus main body connected to the ultrasound probe, in which the diagnostic apparatus main body includes an image generation unit that generates an ultrasound image based on a reception signal acquired by using the ultrasound probe, a monitor with a touch sensor that displays the ultrasound image, a microphone for inputting a voice, and a voice recognition unit that recognizes a voice which is input via the microphone, and the diagnostic apparatus main body sets a normal screen display mode in which the ultrasound image generated by the image generation unit and an operation panel for operating the ultrasound diagnostic apparatus are displayed on the monitor until a predetermined first voice is recognized by the voice recognition unit, sets a transition mode for transition from the normal screen display mode to a full-screen display mode in which an operation of the ultrasound diagnostic apparatus using a voice is possible and only the ultrasound image is displayed on the monitor in a case where the first voice is recognized by the voice recognition unit, sets the full-screen display mode in a case where the voice is recognized by the voice recognition unit in the transition mode, and returns the ultrasound diagnostic apparatus from the full-screen display mode to the normal screen display mode in a case where a predetermined second voice different from the first voice is recognized by the voice recognition unit in the full-screen display mode.

In the transition mode, a highlight display indicating that transition to the full-screen display mode is possible can be displayed on the monitor.

In this case, the highlight display can be a display of a mark indicating that transition to the full-screen display mode is possible.

Alternatively, the highlight display may be a display that makes a display area of the operation panel translucent.

Further, in the normal screen display mode and the full-screen display mode, operations corresponding to touch operations on a screen of the monitor can be different from each other.

According to another aspect of the present invention, there is provided a control method for a handheld type ultrasound diagnostic apparatus including an ultrasound probe and a diagnostic apparatus main body connected to the ultrasound probe, the method including: generating an ultrasound image based on a reception signal acquired by using the ultrasound probe and recognizing a voice which is input; setting a normal screen display mode in which the generated ultrasound image and an operation panel for operating the ultrasound diagnostic apparatus are displayed on a monitor of the diagnostic apparatus main body until a predetermined first voice is recognized; setting a transition mode for transition from the normal screen display mode to a full-screen display mode in which an operation of the ultrasound diagnostic apparatus using a voice is possible and only the ultrasound image is displayed on the monitor in a case where the first voice is recognized; setting the full-screen display mode in a case where the voice is recognized in the transition mode; and returning the ultrasound diagnostic apparatus from the full-screen display mode to the normal screen display mode in a case where a predetermined second voice different from the first voice is recognized in the full-screen display mode.

According to still another aspect of the present invention, there is provided a processor for a handheld type ultrasound diagnostic apparatus including an ultrasound probe and a diagnostic apparatus main body connected to the ultrasound probe, the processor being configured to execute a process including: generating an ultrasound image based on a reception signal acquired by using the ultrasound probe and recognizing a voice which is input; setting a normal screen display mode in which the generated ultrasound image and an operation panel for operating the ultrasound diagnostic apparatus are displayed on a monitor of the diagnostic apparatus main body until a predetermined first voice is recognized; setting a transition mode for transition from the normal screen display mode to a full-screen display mode in which an operation of the ultrasound diagnostic apparatus using a voice is possible and only the ultrasound image is displayed on the monitor in a case where the first voice is recognized; setting the full-screen display mode in a case where the voice is recognized in the transition mode; and returning the ultrasound diagnostic apparatus from the full-screen display mode to the normal screen display mode in a case where a predetermined second voice different from the first voice is recognized in the full-screen display mode.

According to the present invention, an ultrasound diagnostic apparatus includes a monitor with a touch sensor that displays an ultrasound image and a voice recognition unit that recognizes a voice which is input via a microphone. A normal screen display mode in which an ultrasound image generated by an image generation unit and an operation panel for operating the ultrasound diagnostic apparatus are displayed on the monitor is set until a predetermined first voice is recognized by the voice recognition unit. A transition mode for transition from the normal screen display mode to a full-screen display mode in which an operation of the ultrasound diagnostic apparatus using a voice is possible and only the ultrasound image is displayed on the monitor is set in a case where the first voice is recognized by the voice recognition unit. The full-screen display mode is set in a case where the voice is recognized by the voice recognition unit in the transition mode. The ultrasound diagnostic apparatus is returned from the full-screen display mode to the normal screen display mode in a case where a predetermined second voice different from the first voice is recognized by the voice recognition unit in the full-screen display mode. Thereby, a user can smoothly perform ultrasound diagnosis.

DESCRIPTION OF THE PREFERRED EMBODIMENTS

Hereinafter, embodiments of the present invention will be described with reference to the accompanying drawings.

Embodiment 1

Figure 1:
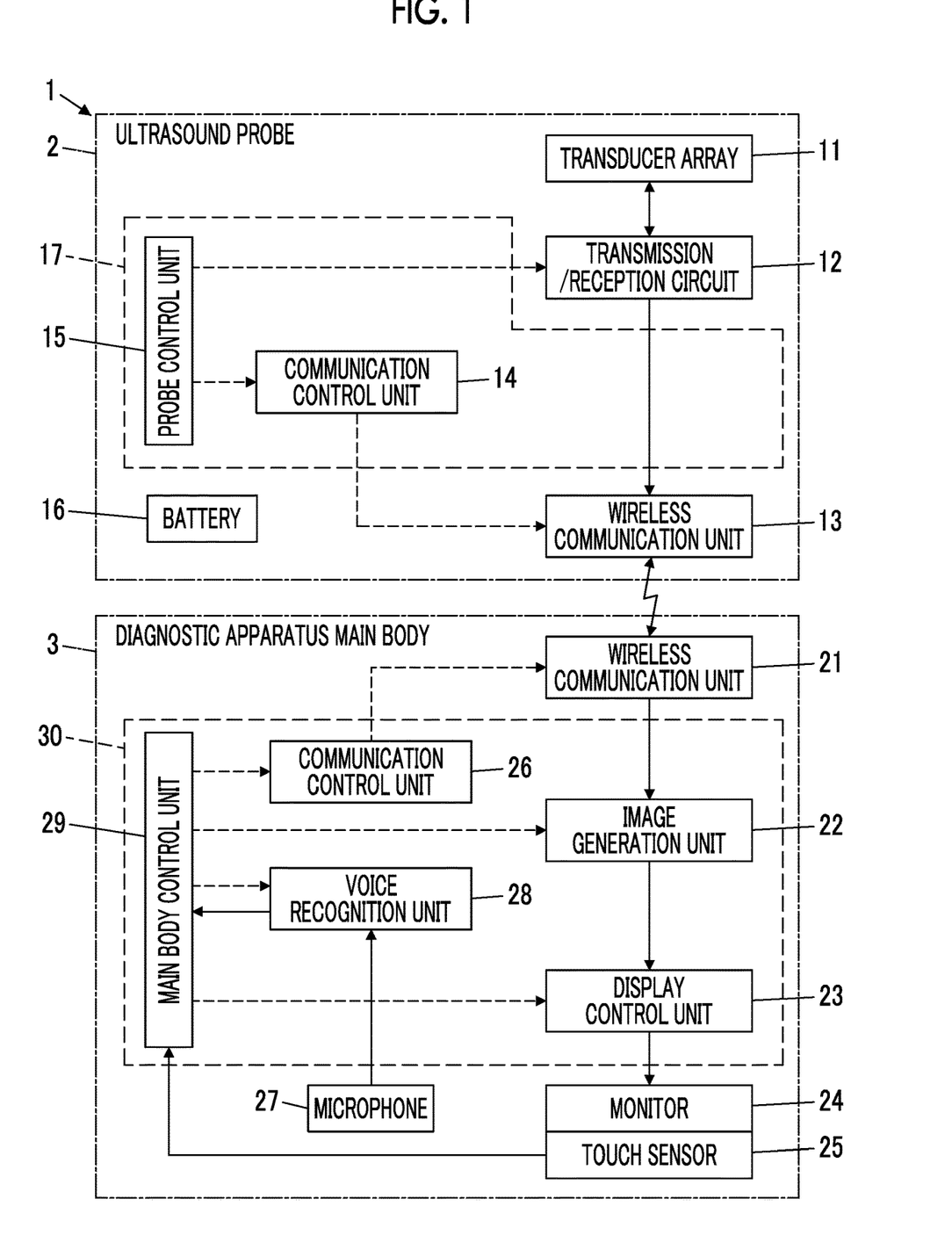
FIG. 1 is a block diagram illustrating a configuration of an ultrasound diagnostic apparatus according to an embodiment 1 of the present invention.

FIG. 1 illustrates a configuration of an ultrasound diagnostic apparatus 1 according to an embodiment 1 of the present invention. As illustrated in FIG. 1, the ultrasound diagnostic apparatus 1 is a so-called portable handheld type ultrasound diagnostic apparatus that includes an ultrasound probe 2 and a diagnostic apparatus main body 3. The ultrasound probe 2 and the diagnostic apparatus main body 3 are connected to each other by wireless communication.

The ultrasound probe 2 includes a transducer array 11, and a transmission/reception circuit 12 and a wireless communication unit 13 are sequentially connected to the transducer array 11. In addition, a communication control unit 14 is connected to the wireless communication unit 13. In addition, a probe control unit 15 is connected to the transmission/reception circuit 12 and the communication control unit 14. In addition, the ultrasound probe 2 includes a battery 16 therein. Further, a probe-side processor 17 is configured by the communication control unit 14 and the probe control unit 15.

The diagnostic apparatus main body 3 includes a wireless communication unit 21, and an image generation unit 22, a display control unit 23, and a monitor 24 are sequentially connected to the wireless communication unit 21. In addition, a touch sensor 25 is disposed by being superimposed on the monitor 24. In addition, a communication control unit 26 is connected to the wireless communication unit 21. In addition, the diagnostic apparatus main body 3 includes a microphone 27, and a voice recognition unit 28 is connected to the microphone 27. In addition, a main body control unit 29 is connected to the image generation unit 22, the display control unit 23, the touch sensor 25, the communication control unit 26, and the voice recognition unit 28.

Further, a main-body-side processor 30 for the ultrasound diagnostic apparatus 1 is configured by the image generation unit 22, the display control unit 23, the communication control unit 26, the voice recognition unit 28, and the main body control unit 29.

The transducer array 11 of the ultrasound probe 2 includes a plurality of ultrasound transducers which are one-dimensionally or two-dimensionally arranged. Each of these transducers transmits an ultrasound wave according to a drive signal supplied from the transmission/reception circuit 12, receives a reflected wave from a subject, and outputs a reception signal. Each transducer is configured by, for example, forming electrodes on both ends of a piezoelectric body such as a piezoelectric ceramic represented by lead zirconate titanate (PZT), a polymeric piezoelectric element represented by poly vinylidene di fluoride (PVDF), or a piezoelectric single crystal represented by lead magnesium niobate-lead titanate (PMN-PT).

Figure 2:
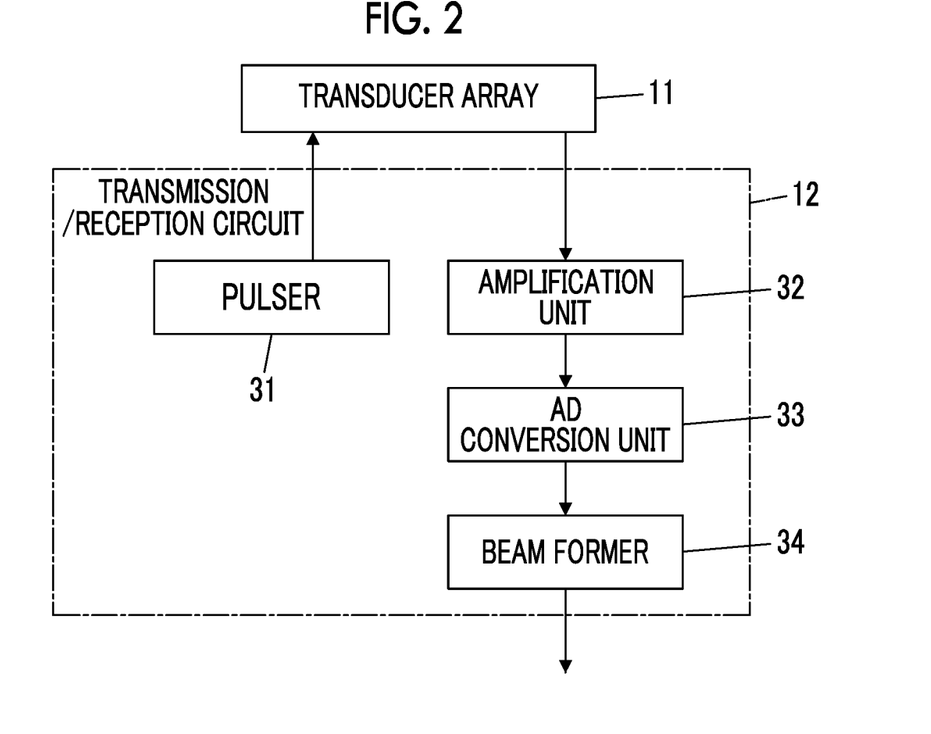
FIG. 2 is a block diagram illustrating an internal configuration of a transmission/reception circuit according to the embodiment 1 of the present invention.

The transmission/reception circuit 12 transmits an ultrasound wave from the transducer array 11 and generates a sound ray signal based on the reception signal acquired by the transducer array 11 under a control of the probe control unit 15. As illustrated in FIG. 2, the transmission/reception circuit 12 includes a pulser 31 connected to the transducer array 11, an amplification unit 32 connected in series from the transducer array 11, an analog-to-digital (AD) conversion unit 33, and a beam former 34.

The pulser 31 includes, for example, a plurality of pulse generators, adjusts a delay amount of each drive signal based on a transmission delay pattern which is selected according to a control signal from the probe control unit 15 such that ultrasound waves to be transmitted from the plurality of transducers of the transducer array 11 form ultrasound beams, and supplies each drive signal with the adjusted delay amount to the plurality of transducers. In this way, in a case where a voltage having a pulse shape or a continuous wave shape is applied to the electrodes of the transducers of the transducer array 11, the piezoelectric body expands and contracts. Thereby, ultrasound waves having a pulse shape or a continuous wave shape are generated from each transducer, and thus an ultrasound beam is formed from a composite wave of these ultrasound waves.

The transmitted ultrasound beam is reflected by an object such as a portion of a subject, and an ultrasound echo propagates toward the transducer array 11 of the ultrasound probe 2. The ultrasound echo which propagates toward the transducer array 11 in this way is received by each transducer included in the transducer array 11. At this time, in a case where the propagating ultrasound echo is received, each transducer included in the transducer array 11 expands and contracts. Thereby, a reception signal as an electrical signal is generated, and these reception signals are output to the amplification unit 32.

The amplification unit 32 amplifies the signal which is input from each transducer included in the transducer array 11, and transmits the amplified signal to the AD conversion unit 33. The AD conversion unit 33 converts the signal transmitted from the amplification unit 32 into pieces of digital reception data, and transmits the pieces of reception data to the beam former 34. The beam former 34 performs so-called reception focus processing by applying and adding a delay to each of the pieces of reception data which is converted by the AD conversion unit 33 according to a sound velocity or a sound velocity distribution which is set based on a reception delay pattern selected according to a control signal from the probe control unit 15. By this reception focus processing, a sound ray signal obtained by performing phasing addition on each of the pieces of reception data which is converted by the AD conversion unit 33 and narrowing down a focus of the ultrasound echo is acquired.

The wireless communication unit 13 of the ultrasound probe 2 is configured by a circuit and the like including an antenna for transmitting and receiving radio waves, and performs wireless communication with the wireless communication unit 21 of the diagnostic apparatus main body 3. At this time, the wireless communication unit 13 of the ultrasound probe 2 generates a transmission signal representing the sound ray signal by modulating carriers based on the sound ray signal generated by the transmission/reception circuit 12, and wirelessly transmits the generated transmission signal to the wireless communication unit 21 of the diagnostic apparatus main body 3. As the carrier modulation method, for example, amplitude shift keying (ASK), phase shift keying (PSK), quadrature phase shift keying (QPSK), 16 quadrature amplitude modulation (16 QAM), or the like is used.

The probe control unit 15 controls each unit of the ultrasound probe 2 based on a program or the like stored in advance. In addition, the probe control unit 15 can transmit the ultrasound beam and receive the ultrasound echo according to any one of a plurality of examination modes by controlling the transmission/reception circuit 12. Here, the examination mode indicates any one of examination modes that can be used in the ultrasound diagnostic apparatus 1, such as a B (brightness) mode, an M (motion) mode, a CD (color doppler) mode, a PD (power doppler) mode, a PW (pulse doppler) mode, or a CW (continuous wave doppler) mode.

The communication control unit 14 controls the wireless communication unit 13 of the ultrasound probe 2 such that the sound ray signal is transmitted at a transmission radio wave strength which is set by the probe control unit 15.

The battery 16 is included in the ultrasound probe 2, and supplies power to each circuit of the ultrasound probe 2.

The wireless communication unit 21 of the diagnostic apparatus main body 3 is configured by a circuit and the like including an antenna for transmitting and receiving radio waves, and performs wireless communication with the wireless communication unit 13 of the ultrasound probe 2. At this time, the wireless communication unit 21 of the diagnostic apparatus main body 3 receives, for example, the transmission signal representing a sound ray signal which is wirelessly transmitted from the wireless communication unit 13 of the ultrasound probe 2 via the antenna, demodulates the received transmission signal, and outputs the sound ray signal.

The communication control unit 26 of the main-body-side processor 30 controls the wireless communication unit 21 of the diagnostic apparatus main body 3 such that the transmission signal is received from the wireless communication unit 13 of the ultrasound probe 2.

Figure 3:
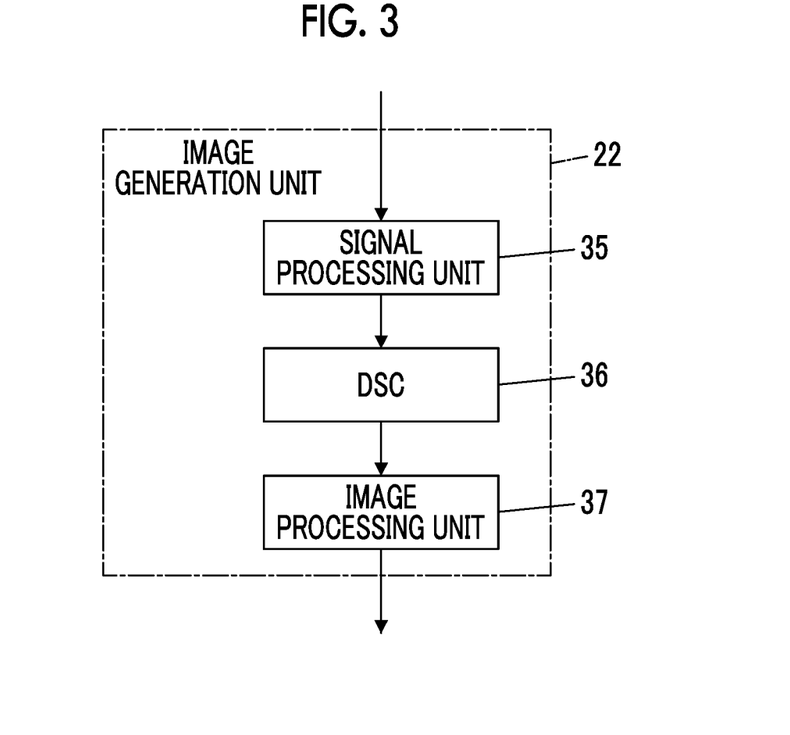
FIG. 3 is a block diagram illustrating an internal configuration of an image generation unit according to the embodiment 1 of the present invention.

As illustrated in FIG. 3, the image generation unit 22 has a configuration in which a signal processing unit 35, a digital scan converter (DSC) 36, and an image processing unit 37 are connected in series.

The signal processing unit 35 generates a B mode image signal, which is tomographic image information related to tissues in the subject, by performing correction of attenuation due to a distance according to a depth of a reflection position of the ultrasound wave and then performing envelope detection processing, on the sound ray signal which is generated by the beam former 34 of the transmission/reception circuit 12 and is received by the wireless communication unit 21.

The DSC 36 converts (raster-converts) the B mode image signal generated by the signal processing unit 35 into an image signal conforming to a normal television signal scanning method.

The image processing unit 37 performs required various image processing such as gradation processing on the B mode image signal which is input from the DSC 36, and then outputs the B mode image signal to the display control unit 23. In the following, the B mode image signal obtained by performing image processing by the image processing unit 37 is simply referred to as an ultrasound image.

Under a control of the main body control unit 29, the display control unit 23 displays the ultrasound image on the monitor 24 by performing predetermined processing on the ultrasound image generated by the image generation unit 22. Further, the display control unit 23 displays, on the monitor 24, an operation panel or the like for allowing a user to perform an input operation, in addition to the ultrasound image.

The monitor 24 displays the ultrasound image and the like, and includes a display device such as a liquid crystal display (LCD) or an organic electroluminescence (EL) display.

The touch sensor 25 is disposed by being superimposed on the display screen of the monitor 24, and allows a user to perform an input operation by a so-called touch operation by bringing a finger, a stylus pen, or the like into contact with or into close to the display screen of the monitor 24. Information which is input by the user via the touch sensor 25 is transmitted to the main body control unit 29.

The microphone 27 is attached to the diagnostic apparatus main body 3, and is for inputting a voice of a user.

The voice recognition unit 28 recognizes a voice of a user that is input via the microphone 27. For example, the voice recognition unit 28 recognizes a voice of a user, and generates voice recognition information as a text string or the like. The voice recognition information generated in this way is transmitted to the main body control unit 29.

The main body control unit 29 controls each unit of the diagnostic apparatus main body 3 based on the program stored in advance, the input operation of the user via the touch sensor 25, and voice recognition information from the voice recognition unit 28.

Figure 4:
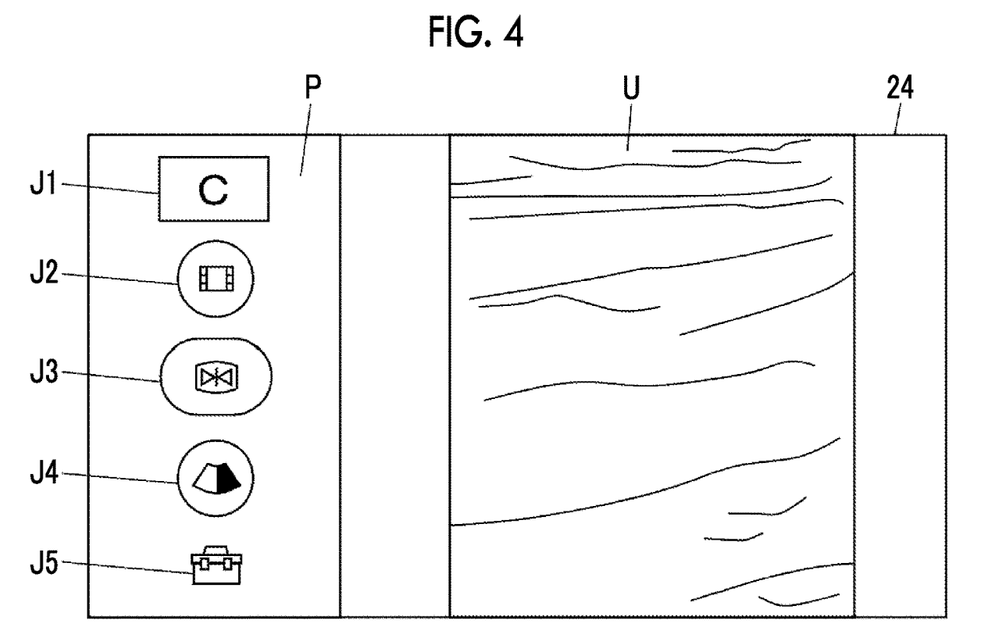
FIG. 4 is a diagram schematically illustrating a display example of a monitor in a case of a normal screen display mode according to the embodiment 1 of the present invention.
Figure 5:
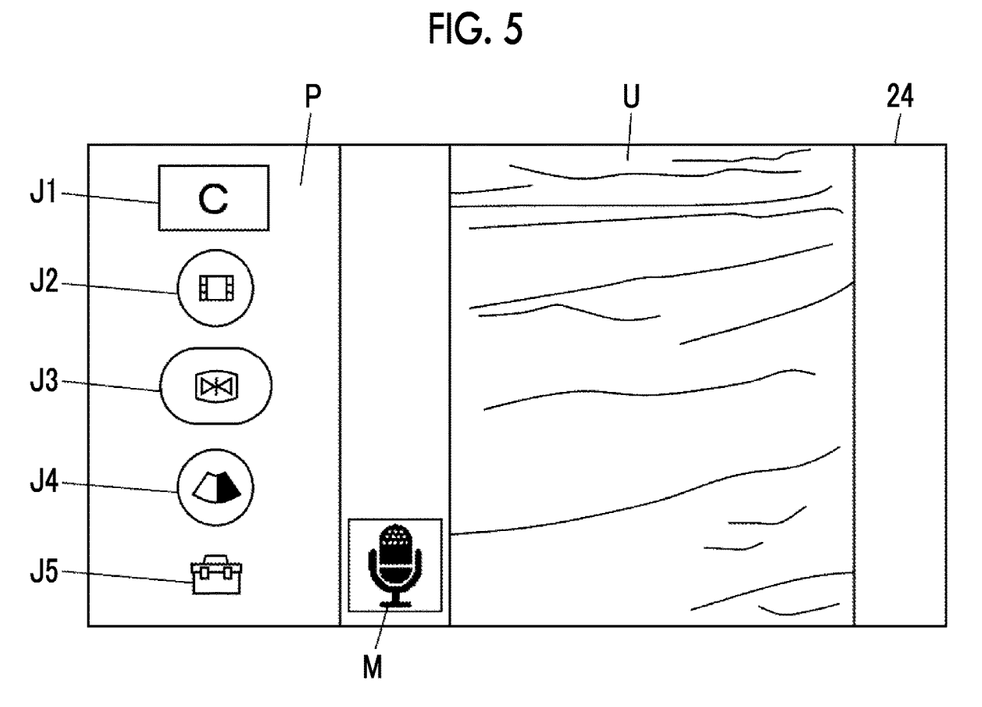
FIG. 5 is a diagram schematically illustrating a display example of the monitor in a case of a transition mode according to the embodiment 1 of the present invention.
Figure 6:
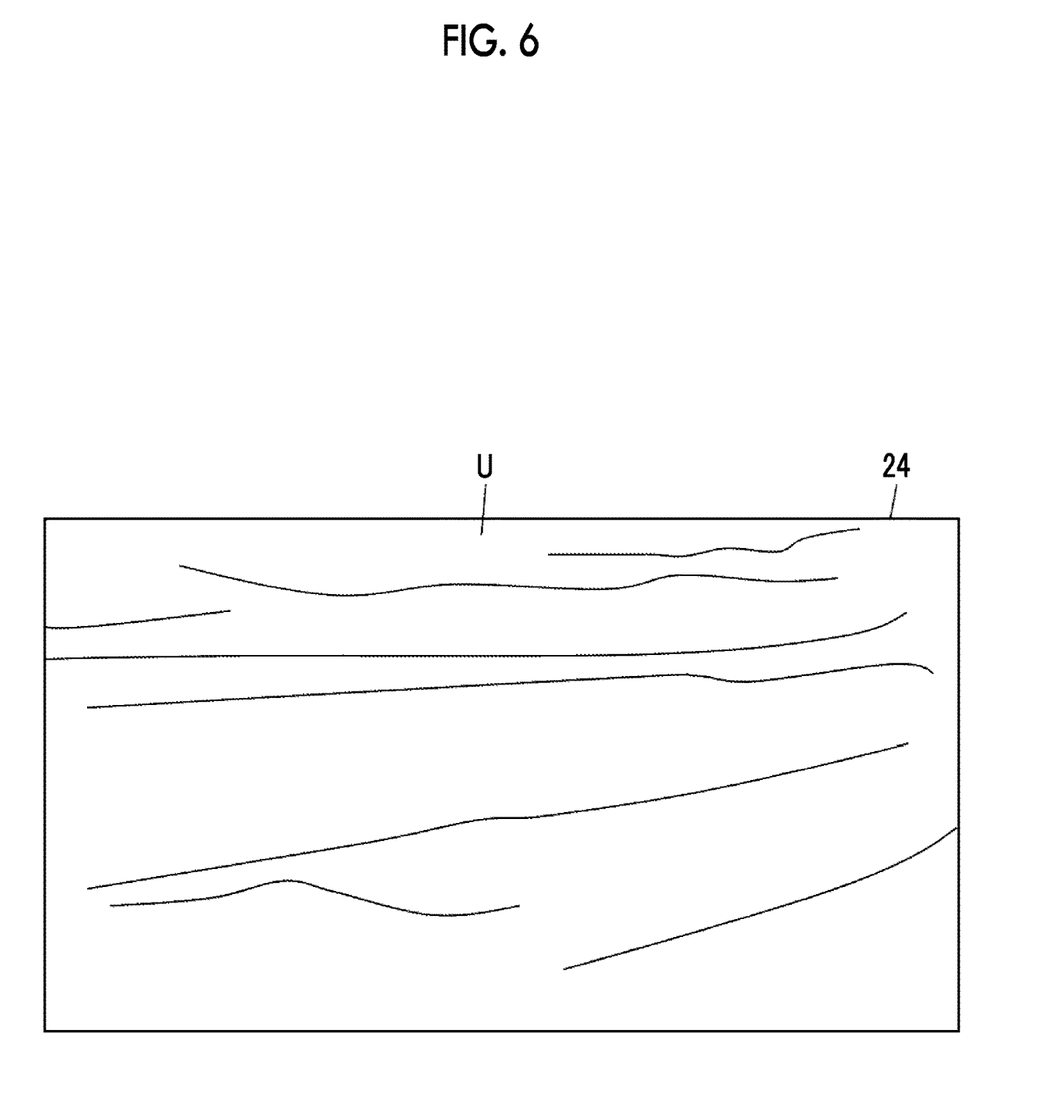
FIG. 6 is a diagram schematically illustrating a display example of the monitor in a case of a full-screen display mode according to the embodiment 1 of the present invention.

In particular, based on the input operation of the user via the touch sensor 25 or based on voice recognition performed on the voice of the user that is input via the microphone 27 by the voice recognition unit 28, the main body control unit 29 performs mode switching between a normal screen display mode in which normal screen display illustrated in FIG. 4 is performed on the monitor 24, a transition mode in which transition screen display illustrated in FIG. 5 is performed on the monitor 24 and an operation of the ultrasound diagnostic apparatus 1 by the voice of the user via the microphone 27 is possible, and a full-screen display mode in which full-screen display illustrated in FIG. 6 is performed on the monitor 24 and an operation of the ultrasound diagnostic apparatus 1 by the voice via the microphone 27 is possible.

The normal screen display mode is, as illustrated in FIG. 4, a mode in which normal screen display including an ultrasound image U generated by the image generation unit 22 and an operation panel P for operating the ultrasound diagnostic apparatus 1 is performed on the monitor 24. The operation panel P includes a plurality of operation icons J1 to J5 for causing the ultrasound diagnostic apparatus 1 to perform a predetermined input operation. In a case where any one of the plurality of operation icons J1 to J5 is touched by the user, an operation corresponding to the any one of the touched operation icons J1 to J5 is performed.

For example, the operation icon J1 is for switching the examination mode, and the operation icon J2 is for storing the ultrasound images U including a plurality of frames continuously generated within a certain time period. The operation icon J3 is for freeze-displaying the ultrasound image U on the monitor 24, the operation icon J4 is for changing a so-called gain and a depth, and the operation icon J5 is for displaying a plurality of other operation icons on the monitor 24.

The transition mode is a mode for transition to the full-screen display. For example, as illustrated in FIG. 5, in addition to the operation panel P and the ultrasound image U, a transition screen display including a mark M for informing the user that voice recognition is possible is performed on the monitor 24.

The full-screen display mode is, for example, as illustrated in FIG. 6, a mode in which the operation of the ultrasound diagnostic apparatus 1 is performed by the voice of the user via the microphone 27 while performing a full-screen display in which the operation panel P and the mark M are not displayed and the ultrasound image U is enlarged and displayed on the entire display screen of the monitor 24.

Here, each of the probe-side processor 17 in the ultrasound probe 2 and the main-body-side processor 30 in the diagnostic apparatus main body 3 is configured with a central processing unit (CPU) and a control program for causing the CPU to perform various processing, the probe-side processor 17 including the communication control unit 14 and the probe control unit 15, and the main-body-side processor 30 including the image generation unit 22, the display control unit 23, the communication control unit 26, the voice recognition unit 28, and the main body control unit 29. On the other hand, each of the probe-side processor 17 and the main-body-side processor 30 may be configured by using a field programmable gate array (FPGA), a digital signal processor (DSP), an application specific integrated circuit (ASIC), a graphics processing unit (GPU), or other integrated circuits (IC), or may be configured by using a combination thereof.

In addition, the communication control unit 14 and the probe control unit 15 of the probe-side processor 17 can be partially or wholly integrated into one CPU or the like. In addition, the image generation unit 22, the display control unit 23, the communication control unit 26, the voice recognition unit 28, and the main body control unit 29 of the main-body-side processor 30 can also be partially or wholly integrated into one CPU or the like.

Figure 7:
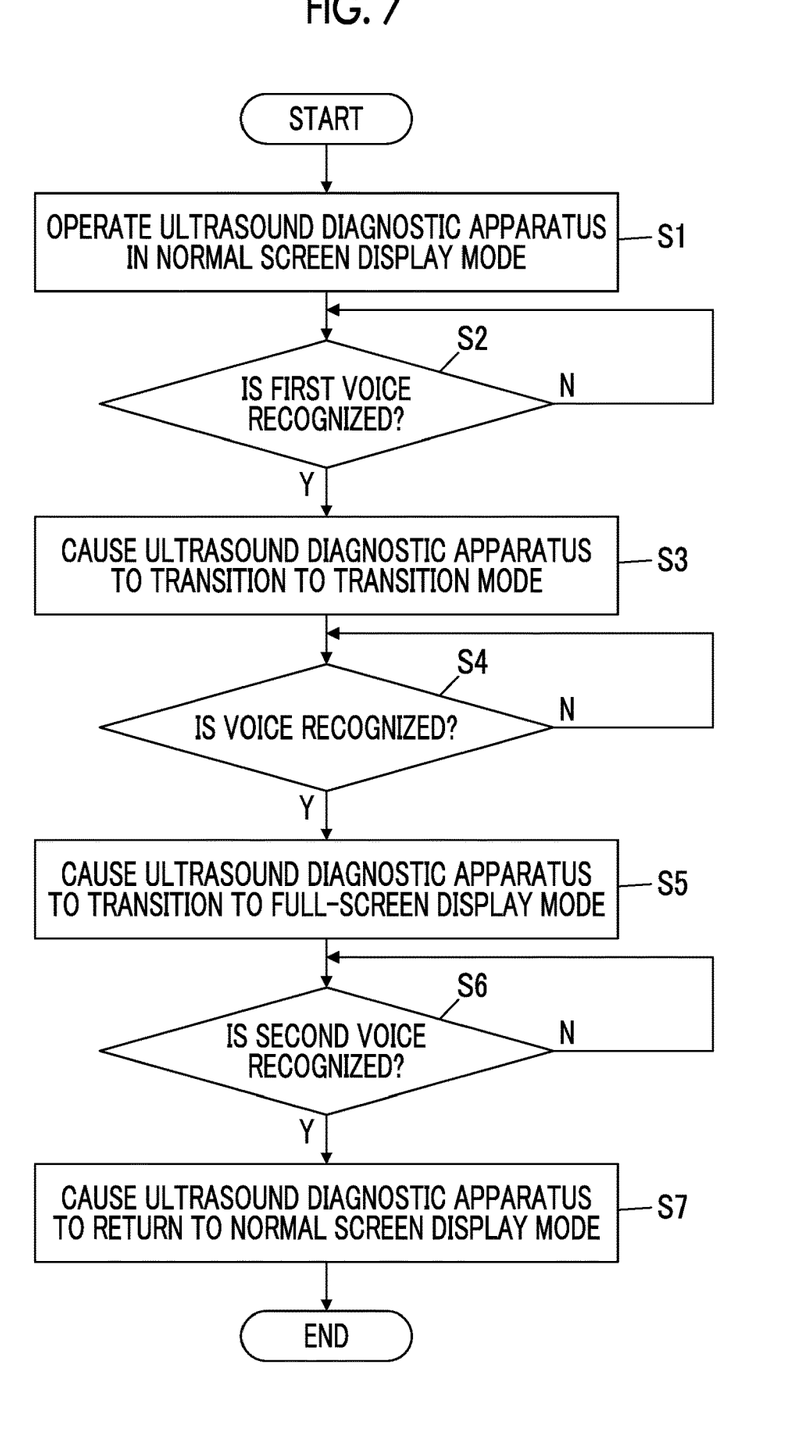
FIG. 7 is a flowchart illustrating an operation of the ultrasound diagnostic apparatus according to the embodiment 1 of the present invention.

Next, an operation in a case where the ultrasound diagnostic apparatus 1 according to the embodiment 1 of the present invention performs switching between the normal screen display mode, the transition mode, and the full-screen display mode will be described using a flowchart of FIG. 7.

First, in a case where ultrasound diagnosis of a subject is started by an input operation or the like of a user via the touch sensor 25, in step S1, the main body control unit 29 operates the ultrasound diagnostic apparatus 1 in the normal screen display mode. At this time, normal screen display as illustrated in FIG. 4 is performed on the monitor 24.

In step S2, the main body control unit 29 determines whether or not a specific first voice such as "Transition to the voice recognition mode" is recognized by the voice recognition unit 28. At this time, the voice recognition unit 28 generates, for example, voice recognition information as a text string or the like by recognizing the voice of the user. The main body control unit 29 determines whether or not the voice recognition information generated by the voice recognition unit 28 corresponds to the first voice. In a case where the voice recognition information corresponds to the first voice, the main body control unit 29 determines that the first voice is recognized by the voice recognition unit 28. In addition, in a case where the voice recognition information does not correspond to the first voice, the main body control unit 29 determines that the first voice is not recognized by the voice recognition unit 28.

Here, in a case where it is determined that the first voice is not recognized, the determination in step S2 is performed again. In this way, the operation in the normal screen display mode is maintained until it is determined that the first voice is recognized.

In step S2, in a case where it is determined that the first voice is recognized, the process proceeds to step S3.

In step S3, the main body control unit 29 causes the ultrasound diagnostic apparatus 1 to transition from the normal screen display mode to the transition mode. In addition, at this time, a transition screen display as illustrated in FIG. 5 is performed on the monitor 24. Here, in the transition screen display, a highlight display indicating that transition to the full-screen display mode is possible is performed. For example, a mark M indicating that transition to the full-screen display mode is possible and voice recognition is possible is displayed on the monitor 24. Thereby, the user can easily recognize a state where voice recognition is possible.

Subsequently, in step S4, the main body control unit 29 determines whether or not a voice uttered by the user is recognized by the voice recognition unit 28. At this time, the main body control unit 29 can determine whether or not the voice recognition unit 28 recognizes the voice by analyzing the voice recognition information generated by the voice recognition unit 28.

In a case where it is determined in step S4 that the voice of the user is not recognized, the determination in step S4 is performed again. In this way, the transition mode is maintained until it is determined that the voice of the user is recognized, and the ultrasound diagnostic apparatus 1 is in a standby state for voice recognition.

In step S4, in a case where it is determined that the voice of the user is recognized, the process proceeds to step S5.

In step S5, the main body control unit 29 causes the ultrasound diagnostic apparatus 1 to transition from the transition mode to the full-screen display mode. At this time, a full-screen display as illustrated in FIG. 6 is performed on the monitor 24. Thereby, for example, even in a case where a size of the monitor 24 is small and thus it is difficult for the user to confirm the ultrasound image U displayed on the monitor 24 in detail in the normal screen display and the transition screen display, the ultrasound image U is enlarged and displayed on the entire display screen of the monitor 24, and thus the user can confirm the ultrasound image U in detail.

In addition, the main body control unit 29 analyzes the voice recognition information generated by the voice recognition unit 28 based on the voice of the user that is input in step S4 and the voice of the user that is newly input in step S5, and controls the ultrasound diagnostic apparatus 1 such that an operation corresponding to the voice recognition information is performed.

Subsequently, in step S6, the main body control unit 29 determines whether or not the voice recognition unit 28 recognizes a specific second voice such as "Transition to the normal screen display mode" by using the same method as the determination in step S2. In a case where it is determined in step S6 that the second voice is not recognized, the determination in step S6 is performed again. In this way, the operation in the full-screen display mode is maintained until it is determined that the second voice is recognized.

In step S6, in a case where it is determined that the second voice is recognized, the process proceeds to step S7.

In step S7, the main body control unit 29 causes the ultrasound diagnostic apparatus 1 to return from the full-screen display mode to the normal screen display mode.

In this way, the operation of performing switching between the normal screen display mode, the transition mode, and the full-screen display mode is completed.

On the other hand, for example, in a medical site at a remote place away from a hospital, such as a site for home nursing, a so-called handheld type ultrasound diagnostic apparatus including an ultrasound probe and a portable diagnostic apparatus main body connected to the ultrasound probe may be used. In such a handheld type ultrasound diagnostic apparatus, the diagnostic apparatus main body often includes a monitor with a touch sensor. Such a monitor has a small size in many cases, and it is necessary to display a user interface for allowing a user to perform an input operation on the monitor in addition to the captured ultrasound image. For this reason, it may be difficult for the user to confirm the ultrasound image displayed on the monitor, and it may be difficult to smoothly perform ultrasound diagnosis.

In the ultrasound diagnostic apparatus 1 according to the embodiment 1 of the present invention, even in a case where both hands of the user are not available during an examination of a subject, it is possible to easily operate the ultrasound diagnostic apparatus 1 by voice recognition. Further, the ultrasound diagnostic apparatus 1 is caused to transition from the transition mode to the full-screen display mode in which the ultrasound image U is enlarged and displayed on the entire display screen of the monitor 24. Thereby, even in a case where the size of the monitor 24 is small, the user can confirm the ultrasound image U in detail. Therefore, according to the ultrasound diagnostic apparatus 1 according to the embodiment 1 of the present invention, the user can smoothly perform ultrasound diagnosis.

In the ultrasound diagnostic apparatus 1, the image generation unit 22 is included in the main-body-side processor 30 of the diagnostic apparatus main body 3. On the other hand, the image generation unit 22 may be included in the probe-side processor 17 of the ultrasound probe 2. In this case, an ultrasound image U is generated in the ultrasound probe 2, and the generated ultrasound image U is wirelessly transmitted from the ultrasound probe 2 to the diagnostic apparatus main body 3. On the other hand, the ultrasound image U is displayed on the monitor 24 in the same manner as in the case where the image generation unit 22 is included in the main-body-side processor 30 of the diagnostic apparatus main body 3.

Further, the ultrasound probe 2 and the diagnostic apparatus main body 3 are connected to each other by wireless communication. On the other hand, the communication is not limited to wireless communication, and the ultrasound probe 2 and the diagnostic apparatus main body 3 can also be connected to each other by so-called wired communication.

Further, in the full-screen display mode, the main body control unit 29 controls the ultrasound diagnostic apparatus 1 such that an operation is performed according to the voice of the user that is recognized by the voice recognition unit 28. On the other hand, for example, in a case where a list in which the voice recognized by the voice recognition unit 28 and the operation of the ultrasound diagnostic apparatus 1 are associated with each other is stored in advance, the ultrasound diagnostic apparatus 1 can be controlled based on the list. For example, in a case where the voice recognition unit 28 recognizes any voice of "freeze", "pause", and "stop", the main body control unit 29 freeze-displays the ultrasound image U on the monitor 24. In a case where the voice recognition unit 28 recognizes any voice of "moving image", "movie", and "clip", the main body control unit 29 can store the ultrasound images U including a plurality of frames generated up to a timing when a certain time is elapsed from the present.

In step S2 and step S3, the ultrasound diagnostic apparatus 1 is caused to transition from the normal screen display mode to the transition mode by being triggered by recognition of the first voice. On the other hand, the trigger for the transition from the normal screen display mode to the transition mode is not limited to recognition of the first voice. For example, a touch operation such as a so-called double tap in which the monitor 24 is tapped twice in a row may be set as a trigger. On the other hand, in a case where the ultrasound diagnostic apparatus 1 is caused to transition from the normal screen display mode to the transition mode by being triggered by recognition of the first voice, the user can cause the ultrasound diagnostic apparatus 1 to transition to the transition mode without using a hand. Therefore, in a case where both hands of the user are not available, it is particularly useful to use the recognition of the first voice as a trigger for the transition to the transition mode.

Figure 8:
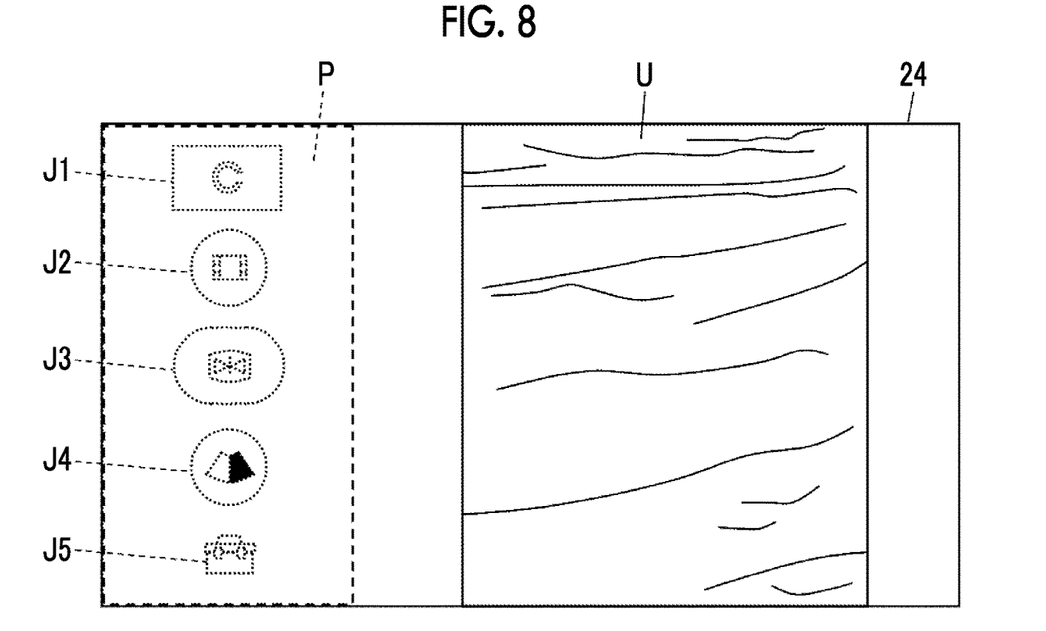
FIG. 8 is a diagram schematically illustrating a display example of the monitor in a case of a transition mode according to a modification example of the embodiment 1 of the present invention.

In addition, as described above, in a case where the ultrasound diagnostic apparatus 1 transitions to the transition mode in step S3, the mark M is displayed on the monitor 24 as a highlight display for informing the user that transition to the full-screen display mode is possible. On the other hand, the highlight display is not limited thereto. For example, as illustrated in FIG. 8, as the highlight display, a display that makes a display area of the operation panel P translucent can be performed. Even in a case where the operation panel P is translucent, it is possible to inform the user that transition to the full-screen display mode is possible.

Further, although not illustrated, the mark M can be displayed while performing the display that makes the display area of the operation panel P translucent.

Further, in the transition mode, the operation panel P is displayed on the monitor 24, and a touch operation via the operation panel P may be enabled or disabled. On the other hand, in a case where a touch operation is disabled and only an operation of the ultrasound diagnostic apparatus 1 by voice recognition is possible in the transition mode, it is possible to prevent an operation that is unintended by the user from being performed even in a case where the user mistakenly touches the display screen of the monitor 24.

In addition, in step S6 and step S7, the ultrasound diagnostic apparatus 1 is caused to transition from the full-screen display mode to the normal screen display mode by being triggered by recognition of the second voice. On the other hand, the trigger for the transition from the full-screen display mode to the normal screen display mode is not limited to recognition of the second voice. For example, a touch operation such as a double tap may be set as a trigger. On the other hand, in a case where the ultrasound diagnostic apparatus 1 is caused to transition from the full-screen display mode to the normal screen display mode by being triggered by recognition of the second voice, the user can cause the ultrasound diagnostic apparatus 1 to transition to the normal screen display mode without using a hand. Therefore, in a case where both hands of the user are not available, it is particularly useful to use the recognition of the second voice as a trigger for the transition to the normal screen display mode.

In addition, an operation corresponding to a touch operation in the normal screen display mode and an operation corresponding to a touch operation in the full-screen display mode can be made different from each other.

For example, in a case where a so-called single tap of tapping the display screen of the monitor 24 only once is performed on the ultrasound image U in the normal screen display mode, an operation of enlarging the ultrasound image U centering on a position where the single tap is performed and displaying the enlarged ultrasound image U on the monitor 24 can be performed. On the other hand, in a case where a single tap is performed in the full-screen display mode, an operation of storing the ultrasound image U displayed on the monitor 24 can be performed.

In addition, for example, in a case where a double tap is performed in the normal screen display mode, an operation of causing the ultrasound diagnostic apparatus 1 to transition from the normal screen display mode to the transition mode is performed. On the other hand, in a case where a double tap is performed in the full-screen display mode, an operation of storing the ultrasound images U including a plurality of frames generated within a certain period of time for which a certain time is elapsed from the present can be performed.

In this way, an operation corresponding to a touch operation in the normal screen display mode and an operation corresponding to a touch operation in the full-screen display mode can be made different from each other. Thereby, the user can more smoothly perform ultrasound diagnosis.

In addition, the main body control unit 29 can also cause the ultrasound diagnostic apparatus 1 to transition from the transition mode to the normal screen display mode. For example, in a case where the ultrasound diagnostic apparatus 1 is in the transition mode, the ultrasound diagnostic apparatus 1 can be caused to transition from the transition mode to the normal screen display mode by being triggered by recognition of the second voice by the voice recognition unit 28 or the operation of the double tap via the touch sensor 25.

In addition, the main body control unit 29 can also cause the ultrasound diagnostic apparatus 1 to transition from the full-screen display mode to the transition mode. For example, in a case where the ultrasound diagnostic apparatus 1 is in the full-screen display mode, the ultrasound diagnostic apparatus 1 can be caused to transition from the full-screen display mode to the transition mode by being triggered by recognition of a specific third voice such as "End the full-screen display mode" by the voice recognition unit 28.

Embodiment 2

In the ultrasound diagnostic apparatus 1 according to the embodiment 1, the ultrasound probe 2 and the diagnostic apparatus main body 3 with the monitor 24 are directly connected to each other by wireless communication, and the diagnostic apparatus main body 3 includes the main-body-side processor 30. On the other hand, for example, a processor that controls the ultrasound diagnostic apparatus 1 may be provided on a network.

Figure 9:
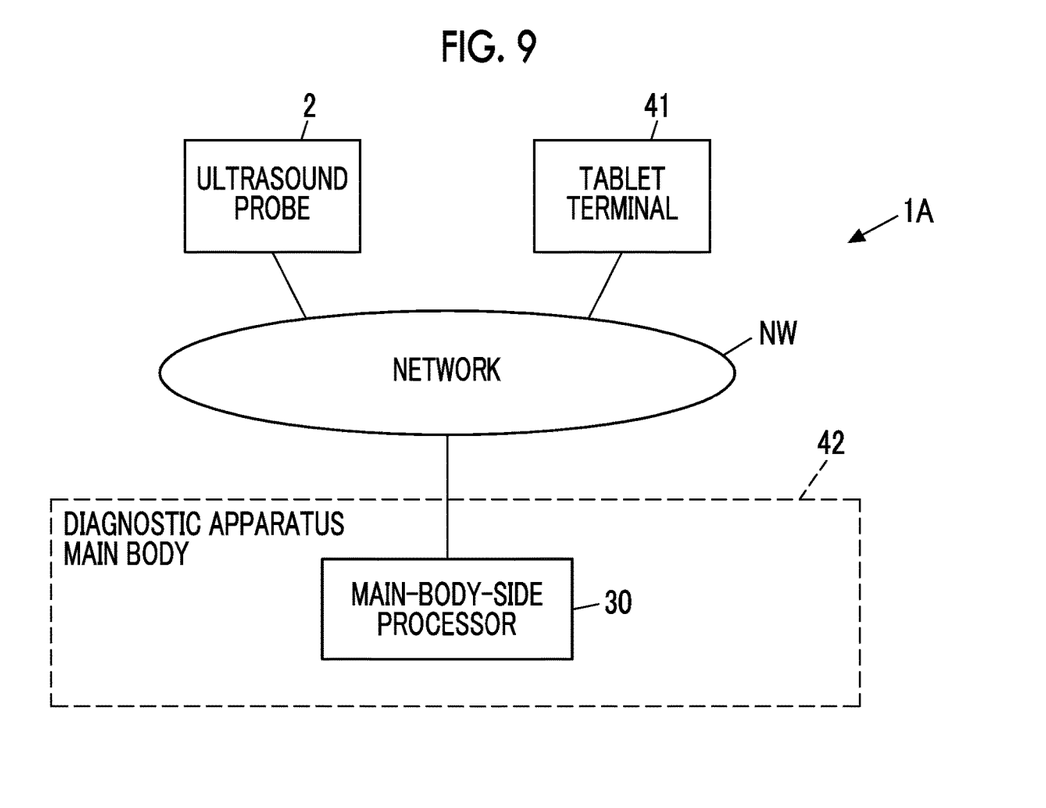
FIG. 9 is a block diagram illustrating a configuration of an ultrasound diagnostic apparatus according to an embodiment 2 of the present invention.

As illustrated in FIG. 9, in an ultrasound diagnostic apparatus 1A according to the embodiment 2, an ultrasound probe 2 and a tablet terminal 41 are connected to a diagnostic apparatus main body 42 via a network NW.

Although not illustrated, the tablet terminal 41 is a portable thin computer including a monitor 24 with a touch sensor 25 and a microphone 27, and corresponds to the diagnostic apparatus main body 3 according to the embodiment 1 illustrated in FIG. 1 from which the main-body-side processor 30 is excluded.

The diagnostic apparatus main body 42 is obtained by excluding the monitor 24, the touch sensor 25, and the microphone 27 from the diagnostic apparatus main body 3 according to the embodiment 1, and includes a main-body-side processor 30.

Even in a case where the ultrasound diagnostic apparatus 1A has such a configuration, as in the ultrasound diagnostic apparatus 1 according to the embodiment 1, switching between the normal screen display mode, the transition mode, and the full-screen display mode can be performed based on the voice recognition by the voice recognition unit 28 or the input operation via the touch sensor 25. Further, in the full-screen display mode, the ultrasound image U is enlarged and displayed on the entire display screen of the monitor 24. Thereby, the user can smoothly perform ultrasound diagnosis.

EXPLANATION OF REFERENCES 1, 1A: ultrasound diagnostic apparatus
2: ultrasound probe
3, 42: diagnostic apparatus main body
11: transducer array
12: transmission/reception circuit
13, 21: wireless communication unit
14, 26: communication control unit
15: probe control unit
16: battery
17: probe-side processor
22: image generation unit
23: display control unit
24: monitor
25: touch sensor
27: microphone
28: voice recognition unit
29: main body control unit
30: main-body-side processor
31: pulser
32: amplification unit
33: AD conversion unit
34: beam former
35: signal processing unit
36: DSC
37: image processing unit
41: tablet terminal
J1 to J5: operation icons
M: mark
NW: network
P: operation panel
U: ultrasound image

What is claimed is:

1. A handheld type ultrasound diagnostic apparatus comprising:
an ultrasound probe; and
a diagnostic apparatus main body connected to the ultrasound probe,
wherein the diagnostic apparatus main body includes
a monitor with a touch sensor,
a microphone configured to input a voice, and
a processor configured to
generate an ultrasound image based on a reception signal acquired by using the ultrasound probe,
display the ultrasound image on the monitor,
recognize the voice which is input via the microphone, and
until a predetermined specific first voice is recognized, be in a normal screen display mode in which the processor is configured to display the ultrasound image and an operation panel for operating the ultrasound diagnostic apparatus on the monitor,
once the predetermined specific first voice is recognized, enter a transition mode for transition from the normal screen display mode to a full-screen display mode in which the processor is configured to enable an operation of the ultrasound diagnostic apparatus using the voice and display only the ultrasound image on the monitor,
in the transition mode, display a highlight display that makes a display area of the operation panel translucent, indicating that transition to the full-screen display mode is possible on the monitor,
once any voice from a user is recognized in the transition mode, enter the full-screen display mode, and
once a predetermined specific second voice different from the predetermined specific first voice is recognized in the full-screen display mode, return from the full-screen display mode to the normal screen display mode.

2. The ultrasound diagnostic apparatus according to claim 1,
wherein, in the normal screen display mode and the full-screen display mode, operations corresponding to touch operations on a screen of the monitor are different from each other.

3. A control method for a handheld type ultrasound diagnostic apparatus including an ultrasound probe and a diagnostic apparatus main body connected to the ultrasound probe, the method comprising:
generating an ultrasound image based on a reception signal acquired by using the ultrasound probe;
until a predetermined specific first voice is recognized, being in a normal screen display mode in which the generated ultrasound image and an operation panel for operating the ultrasound diagnostic apparatus are displayed on a monitor of the diagnostic apparatus main body;
recognizing the predetermined specific first voice;
after recognizing the predetermined specific first voice, entering a transition mode for transition from the normal screen display mode to a full-screen display mode in which an operation of the ultrasound diagnostic apparatus using a voice is possible and only the ultrasound image is displayed on the monitor;
in the transition mode, displaying a highlight display that makes a display area of the operation panel translucent, indicating that transition to the full-screen display mode is possible on the monitor;
recognizing any voice from a user in the transition mode;
after recognizing the any voice, entering the full-screen display mode;
recognizing a predetermined specific second voice different from the predetermined specific first voice in the full-screen display mode; and
after recognizing the predetermined specific second voice, returning from the full-screen display mode to the normal screen display mode.

4. A processor for a handheld type ultrasound diagnostic apparatus including an ultrasound probe and a diagnostic apparatus main body connected to the ultrasound probe, the processor being configured to execute a process comprising:
generating an ultrasound image based on a reception signal acquired by using the ultrasound probe;
until a predetermined specific first voice is recognized, being in a normal screen display mode in which the generated ultrasound image and an operation panel for operating the ultrasound diagnostic apparatus are displayed on a monitor of the diagnostic apparatus main body;
once the predetermined specific first voice is recognized, entering a transition mode for transition from the normal screen display mode to a full-screen display mode in which an operation of the ultrasound diagnostic apparatus using a voice is possible and only the ultrasound image is displayed on the monitor;

in the transition mode, displaying a highlight display that makes a display area of the operation panel translucent, indicating that transition to the full-screen display mode is possible on the monitor;

once any voice from a user is recognized in the transition mode, entering the full-screen display mode in a case where the any voice is recognized in the transition mode;

once a predetermined specific second voice different from the predetermined specific first voice is recognized in the full-screen display mode, returning the ultrasound diagnostic apparatus from the full-screen display mode to the normal screen display mode.

\* \* \* \* \*